(12) United States Patent
Dehghan Niri et al.

(10) Patent No.: US 10,161,910 B2
(45) Date of Patent: Dec. 25, 2018

(54) METHODS OF NON-DESTRUCTIVE TESTING AND ULTRASONIC INSPECTION OF COMPOSITE MATERIALS

(71) Applicant: GENERAL ELECTRIC COMPANY, Schenectady, NY (US)

(72) Inventors: Ehsan Dehghan Niri, Glenville, NY (US); Curtis Wayne Rose, Mechanicville, NY (US); Amir Riahi, Greenville, SC (US); Eric Michael Shain, Simpsonville, SC (US)

(73) Assignee: General Electric Company, Schenectady, NY (US)

( * ) Notice: Subject to any disclaimer, the term of this patent is extended or adjusted under 35 U.S.C. 154(b) by 250 days.

(21) Appl. No.: 14/992,444

(22) Filed: Jan. 11, 2016

(65) Prior Publication Data
US 2017/0199160 A1    Jul. 13, 2017

(51) Int. Cl.
| | |
|---|---|
| *G01B 5/28* | (2006.01) |
| *G01B 5/30* | (2006.01) |
| *G01N 29/06* | (2006.01) |
| *G01N 29/44* | (2006.01) |

(52) U.S. Cl.
CPC ......... *G01N 29/0654* (2013.01); *G01N 29/44* (2013.01); *G01N 2291/023* (2013.01); *G01N 2291/0289* (2013.01)

(58) Field of Classification Search
CPC ............... G01N 29/0654; G01N 29/44; G01N 2291/023; G01N 2291/0289
See application file for complete search history.

(56) References Cited

U.S. PATENT DOCUMENTS

| | | |
|---|---|---|
| 4,694,434 A | 9/1987 | von Ramm et al. |
| 8,965,100 B2 | 2/2015 | Lin et al. |
| 2005/0101864 A1 | 5/2005 | Zheng et al. |

(Continued)

OTHER PUBLICATIONS

Donal B. Downey et al., Clinical Utility of Three-dimensional US, Imaging & Therapeutic Technology, vol. 20, No. 2, Mar.-Apr. 2000, pp. 559-571.

R. A. Smith et al., Automated Non-Destructive Analysis and Advanced 3D Defect Characterisation from Ultrasonic Scans of Composites, Presented at the 17th International Conference on Composite Materials; Jul. 27, 2009; Edinburgh.

(Continued)

*Primary Examiner* — Toan K Le
(74) *Attorney, Agent, or Firm* — McNees Wallace & Nurick LLC

(57) ABSTRACT

A method of non-destructive testing includes locating an ultrasonic transducer with respect to a component having a visually-inaccessible structure to collect B-scan data from at least one B-scan of the component and to collect C-scan data from at least one C-scan of the component. The method also includes filtering the B-scan data and the C-scan data to remove random noise and coherent noise based on predetermined geometric information about the visually-inaccessible structure to obtain filtered data. The method further includes performing linear signal processing and nonlinear signal processing to determine a damage index for a plurality of voxels representing the visually-inaccessible structure from the filtered B-scan data and the filtered C-scan data to generate a V-scan image. A method of non-destructive testing of a wind turbine blade and an ultrasound system are also disclosed.

21 Claims, 13 Drawing Sheets
(3 of 13 Drawing Sheet(s) Filed in Color)

(56) References Cited

U.S. PATENT DOCUMENTS

2006/0130587 A1* 6/2006 Howard ................. G01N 29/07
73/606
2011/0087443 A1* 4/2011 Zhang ................ G01N 29/0654
702/39
2013/0235897 A1* 9/2013 Bouteyre ............... F03D 1/065
374/4

OTHER PUBLICATIONS

H. P. Dietz, Ultrasound imaging of the pelvic floor. Part II: three-dimensional or volume imaging, Ultrasound Obstet Gynecol 2004; 23: 615-625.
Aaron Fenster et al., 3D Ultrasound Imaging in Image-Guided Intervention, Advancements and Breakthroughs in Ultrasound Imaging, http://dx.doi.org/10.5772/55230, copyright 2013.
Luis F. Goncalves et al., Three-and 4-Dimensional Ultrasound in Obstetric Practice Does it Help? J Ultrasound Med 2005; 24: 1599-1624, copyright 2005 by the American Institute of Ultrasound in Medicine.
Aaron Fenster et al., Three-dimensional ultrasound scanning, Interface Focus (2011) 1, 503-519, doi:10.1098/rsfs.2011.0019, published online Jun. 1, 2011, downloaded from http://rsfs.royalsocietypublishing.org/ on Feb. 17, 2015.
Mark S. Sklansky et al., Real-time 3-Dimensional Fetal Echocardiography with an Instantaneous Volume-Rendered Display Early Description and Pictorial Essay, J Ultrasound Med 23:283-289, 2004, copyright 2004 by the American Institute of Ultrasound in Medicine.

* cited by examiner

METHODS OF NON-DESTRUCTIVE TESTING AND ULTRASONIC INSPECTION OF COMPOSITE MATERIALS

FIELD OF THE INVENTION

The present invention is directed to systems and methods of detection. More specifically, the present invention is directed to systems and methods of detecting waviness or debonding in manufactured articles with ultrasound.

BACKGROUND OF THE INVENTION

Layer waviness and debonding are common manufacturing imperfections in thick carbon fiber composite components. Layer waviness may significantly reduce the compression strength of the composite component. For example, waviness in a critical portion of a wind turbine blade, such as the spar cap, may lead to failure of the blade, resulting in the loss of the equipment and power generation capability.

The blade of a wind turbine is primarily loaded in bending due to aerodynamic lift forces. To resist bending, a pair of spar caps are placed as far apart as possible in the flapwise direction on the back sides of the upwind face and the downwind face. The spar caps conventionally include unidirectional fibers running along the length of the blade. To be effective, the spar caps are connected to each other by a shear web made of diagonal fibers.

The problem of waviness may have been a critical issue in reported wind turbine manufacturing instances where the layers of the laminates in carbon composite spar caps were found to be affected by in-plane and/or out-of-plane waviness and disbonds. In order to reliably predict the structural integrity and strength of wind turbine blades with the potential for internal waviness and disbonds, the flaws must be detectable and characterized using a non-destructive testing (NDT) method.

X-ray Computed Tomography (CT) scanning is the most reliable NDT method in terms of detecting fiber waviness. CT images provide detailed information about the fiber distribution that is, so far, not achievable with other NDT techniques. The main advantage of CT imaging is its ability to locate and size planar volumetric details of features in three dimensions. The volumetric information significantly enhances the characterization of features with complex geometries, such as waviness. CT, however, is very expensive, requires significant safety precautions, is not applicable for massive quality control, and is not practical for on-site inspection.

Ultrasonic tests (UTs), on the other hand, have been successfully implemented for field inspections to detect and size debonding, porosity, and voids in composite laminates, but it is unreliable for features with complex shapes. Its detection and characterization abilities for waviness are limited. Traditional A-scans, B-scans, and C-scans only provide two-dimensional (2-D) information of the waviness. Since multiple 2-D B-scan and C-scan images must be integrated mentally to give a sense of any out-of-plane waviness, 2-D viewing of three-dimensional (3-D) complex features, such as waviness, using conventional 2-D B-scans and C-scans, may significantly hamper the ability of such an NDT system to quantify and visualize structures with a complex geometry.

Due to the complex geometry of internal organs and anomalies in the human body, 3-D medical ultrasonic imaging has gained significant attention in the past few years and has played an increasingly important role in diagnosis, minimally invasive image-guided interventions, and intraoperative imaging. Researchers and commercial companies in the medical imaging field, including GE Healthcare (Little Chalfont, UK), are increasingly integrating 3-D visualization into the ultrasonic instrumentation. This advanced imaging tool, however, has not been fully implemented in commercial UT software for routine NDT inspection of critical components.

BRIEF DESCRIPTION OF THE INVENTION

In an embodiment, a method of non-destructive testing includes locating an ultrasonic transducer with respect to a component having a visually-inaccessible structure to collect B-scan data from at least one B-scan of the component and to collect C-scan data from at least one C-scan of the component. The method also includes filtering the B-scan data and the C-scan data to remove random noise and coherent noise based on predetermined geometric information about the visually-inaccessible structure to obtain filtered data. The method further includes performing linear signal processing and nonlinear signal processing to determine a damage index for a plurality of voxels representing the visually-inaccessible structure from the filtered B-scan data and the filtered C-scan data to generate a "V-scan" image.

In another embodiment, a method of non-destructive testing of a wind turbine blade includes directing at least one B-scan of a visually-inaccessible structure of the wind turbine blade by an ultrasonic transducer to collect B-scan data of the visually-inaccessible structure. The method also includes directing at least one C-scan of the visually-inaccessible structure by the ultrasonic transducer to collect C-scan data of the visually-inaccessible structure. The method further includes generating a volume visualization as a "V-scan" image of the visually-inaccessible structure from the B-scan data and the C-scan data.

In another embodiment, an ultrasound system includes at least one ultrasonic transducer and a computer operatively connected to the ultrasonic transducer. The computer is configured to direct the ultrasonic transducer to conduct at least one B-scan and collect B-scan data from the at least one B-scan and to conduct at least one C-scan and collect C-scan data from the at least one C-scan of a component including a visually-inaccessible structure. The computer is also configured to filter the B-scan data and the C-scan data to remove random noise and coherent noise based on predetermined geometric information about the visually-inaccessible structure to obtain filtered data. The computer is further configured to perform linear signal processing and nonlinear signal processing to determine a damage index for a plurality of voxels representing the visually-inaccessible structure from the filtered B-scan data and the filtered C-scan data to generate a "V-scan" image.

Other features and advantages of the present invention will be apparent from the following more detailed description, taken in conjunction with the accompanying drawings which illustrate, by way of example, the principles of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Wherever possible, the same reference numbers will be used throughout the drawings to represent the same parts.

DETAILED DESCRIPTION OF THE INVENTION

Provided are methods and systems for detection of waviness and debonding of a visually-inaccessible structure to determine a damage state of the visually-inaccessible structure.

Embodiments of the present disclosure, for example, in comparison to concepts failing to include one or more of the features disclosed herein, detect out-of-plane waviness, distinguish between debonding and waviness, provide a "V-scan" of a visually-inaccessible structure, provide a volume visualization based on assigning non-zero values to voxels outside the volume of interest, remove coherent noise from ultrasound signals, characterize debonding, characterize waviness, or combinations thereof.

As used herein, "debonding" refers to failure of an adhesive or matrix in a layered component, leading to a disbond in the layered component.

As used herein, "waviness" refers to macroscopic surface or internal layer deviations from a predetermined configuration, such as planar, in a layered component. Waviness may either be in-plane or out-of-plane. In the case of composite fibers, in-plane waviness refers to fibers deviating from the main fiber direction within the plane of a layer, whereas out-of-plane waviness refers to fibers deviating from the plane of the main fiber direction of the layer, i.e. deviating in a thickness direction of the layer.

In some embodiments, the topography of the visually-inaccessible structure includes one or more waves, one or more disbonds, one or more voids, or a combination thereof. In some embodiments, the voids include porosity, wrinkles, dry fibers, depth of a wave, or combinations thereof. In some embodiments, the void volume or the overall part void percentage is determined.

Figure 1:
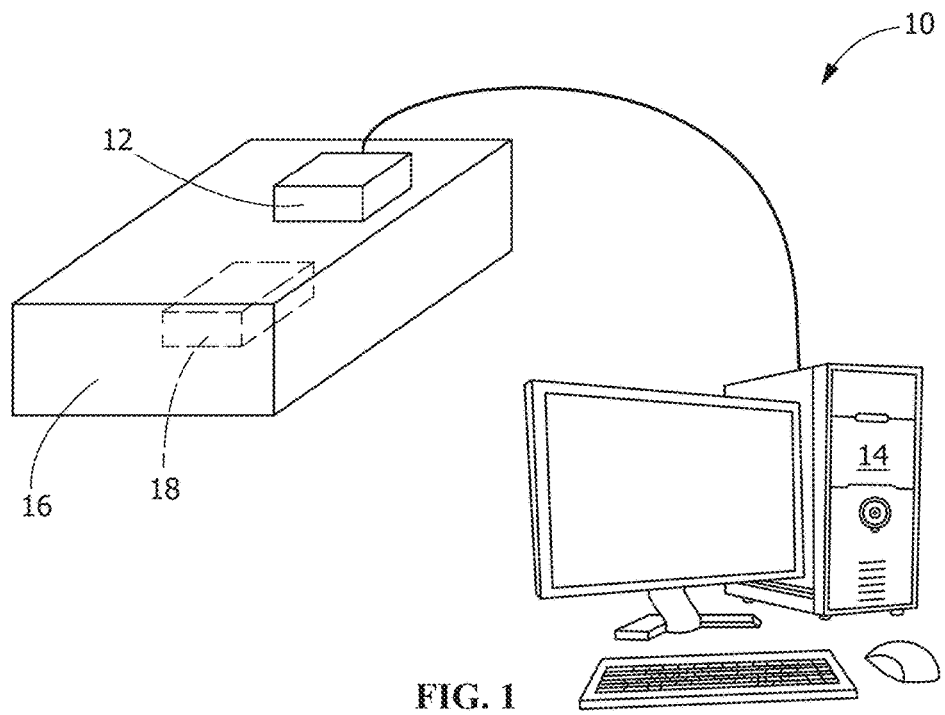
FIG. 1 is a schematic perspective view of an ultrasound system in an embodiment of the present disclosure.

Referring to FIG. 1, an ultrasound system 10 includes at least one ultrasonic transducer 12 and a computer 14 operatively connected to the ultrasonic transducer 12. The computer 14 is configured to direct the ultrasonic transducer 12 to conduct at least one B-scan and collect B-scan data and to conduct at least one C-scan and collect C-scan data of a component 16 including a visually-inaccessible structure 18, filter the B-scan data and the C-scan data to remove random noise and coherent noise based on predetermined geometric information about the visually-inaccessible structure 18 to obtain filtered data, and perform linear signal processing and nonlinear signal processing to determine a damage index for a plurality of voxels representing the visually-inaccessible structure 18 from the filtered B-scan data and the filtered C-scan data. In some embodiments, the computer 14 is configured to perform the above-mentioned tasks by software, hardware, user input, or combinations thereof.

In some embodiments, methods take advantage of known geometric and physical parameters of a visually-inaccessible structure 18 to provide better imaging and characterization of the visually-inaccessible structure 18 based on ultrasound data. In some embodiments, the visually-inaccessible structure 18 is a stationary layered composite structure and the method images and characterizes debonding and waviness, including, but not limited to, out-of-plane waviness, of the visually-inaccessible structure 18. In some embodiments, the visually-inaccessible structure 18 has a known layer thickness and a known layer composition. In some embodiments, the known layer thickness and the known layer composition are used to remove coherent noise from the ultrasound signals.

In some embodiments, B-scan and C-scan ultrasound data of a visually-inaccessible structure 18 are extracted, filtered, and processed to provide a damage index and a volume visualization in the form of a V-scan showing one or more features of the visually-inaccessible structure 18, and the V-scan data is compressed and converted to contour extraction data of detected features. In some embodiments, a method identifies, categorizes, and quantifies any debonding features and waviness features, including, but not limited to, out-of-plane waviness features, in the visually-inaccessible structure 18.

Figure 3:
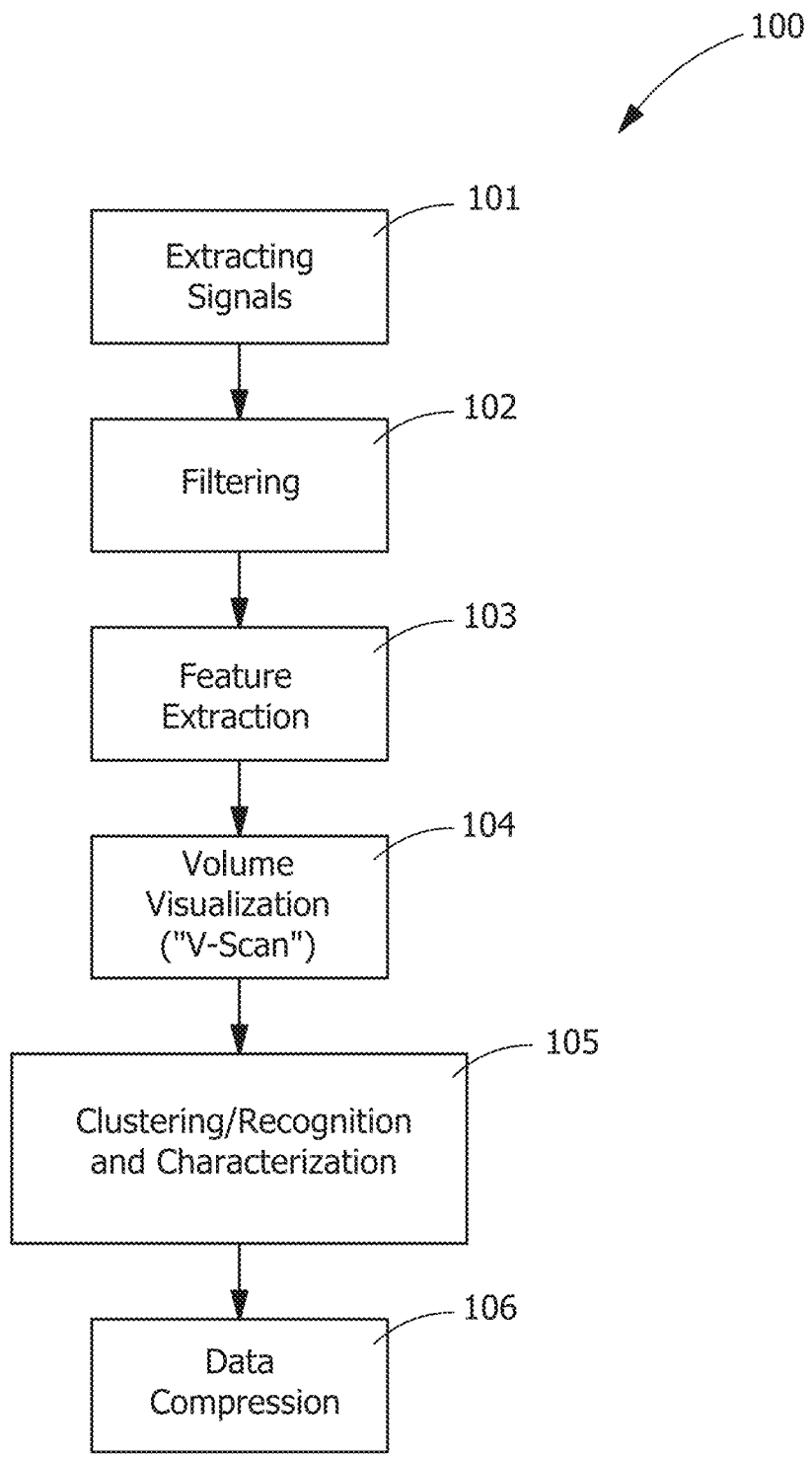
FIG. 3 is a flowchart of a method of detection in an embodiment of the present disclosure.

Referring to FIG. 3, a method 100 includes extracting signals (step 101) from B-scan and C-scan data, filtering (step 102) the extracted signals to get filtered signals, feature extraction (step 103) of the filtered signals to assign a damage index for each voxel representing part of the feature volume, creating a volume visualization as a V-scan (step 104) of the voxel damage data, clustering voxels and distinguishing and characterizing waviness features and debonding features (step 105), and data compression (step 106) by defining contour levels of the features based on geometric information and compressing the data as contours of the 3-dimensional features.

Figure 4:
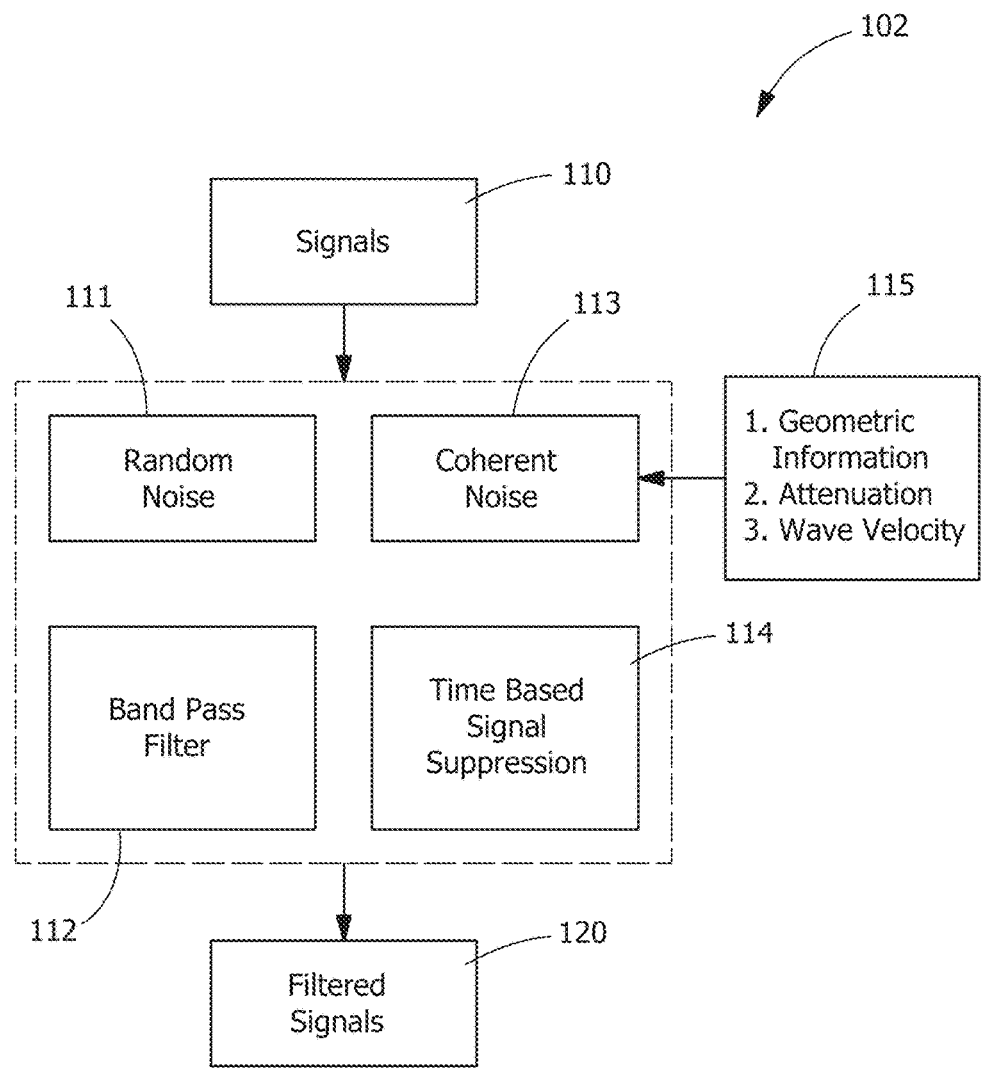
FIG. 4 is a flowchart of the filtering of the method of FIG. 3.

Referring to FIG. 4, the filtering (step 102) of the ultrasound signals 110 to obtain filtered signals 120 preferably includes filtering out random noise 111 using one or more band pass filters 112 but also filtering out coherent noise 113 based on known geometric information 115 about layer thickness and composition. The coherent noise 113 is an unwanted signal arising from reflections of the various layers in the layered composite. Time-based signal suppression 114 is preferably used to remove coherent noise 113 based on wave velocity and attenuation as a result of the known geometric information 115 of a layered geometry.

Figure 5:
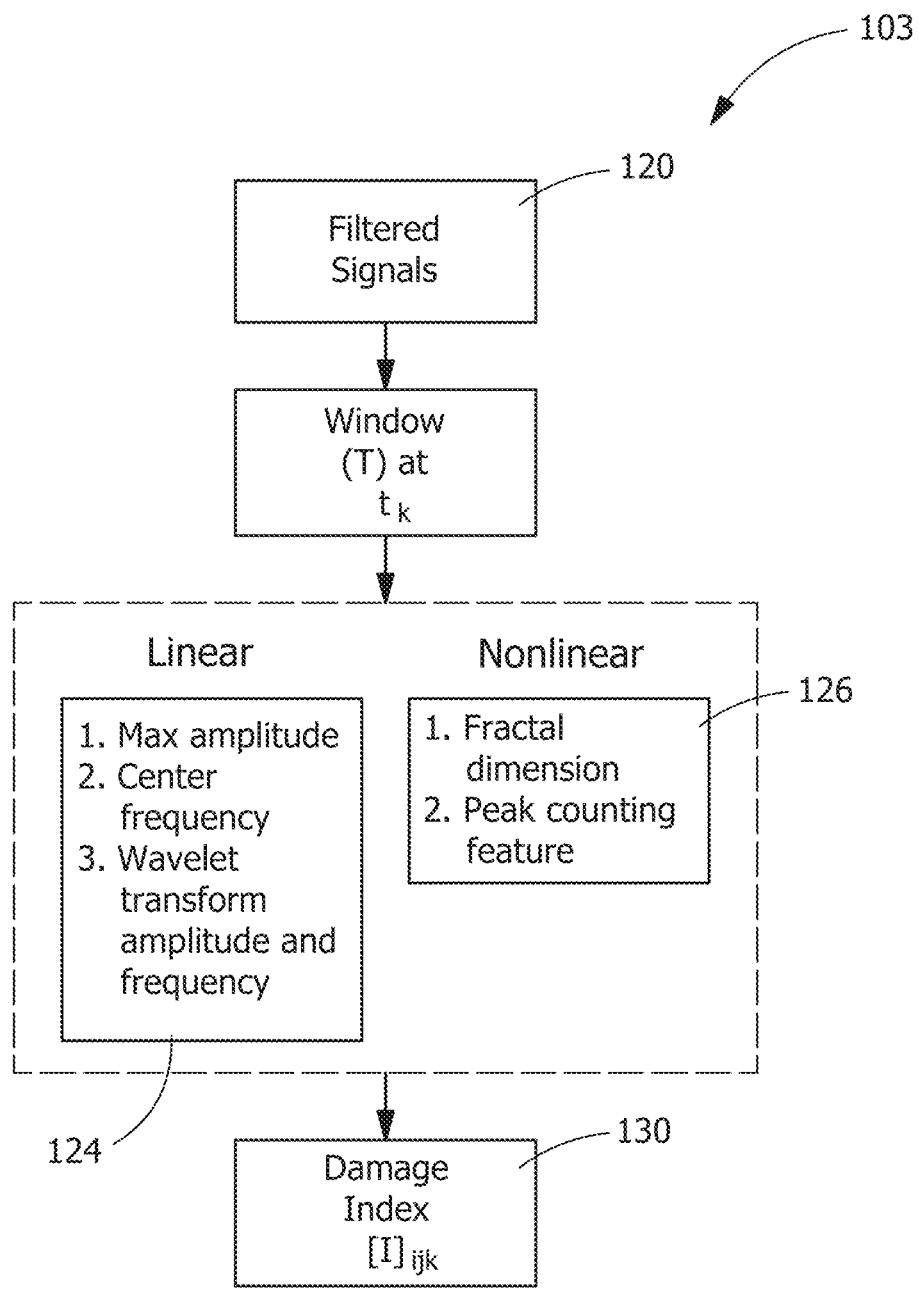
FIG. 5 is a flowchart of the feature extraction of the method of FIG. 3.

Referring to FIG. 5, feature extraction (step 103) of the filtered signals 120 preferably leads to assignment of a damage index value 130 of each voxel representing a unit of volume of the structure. The feature extraction is preferably based on both linear signal processing methods 124 and nonlinear signal processing methods 126. The linear methods 124 may include, but are not limited to, maximum amplitude, center frequency, wavelet transform amplitude and frequency methods, and combinations thereof. The nonlinear methods 126 may include, but are not limited to, fractal dimension, peak counting, and combinations thereof. Peak counting may capture bifurcations, chaos, harmonics, and subharmonics of the signal. The damage index value 130 assigned for each voxel is preferably a function of more than one of these feature extraction methods. In some embodiments, all of the above-mentioned linear methods 124 and nonlinear methods 126 are included in assigning a damage index value 130 to each voxel.

Figure 6:
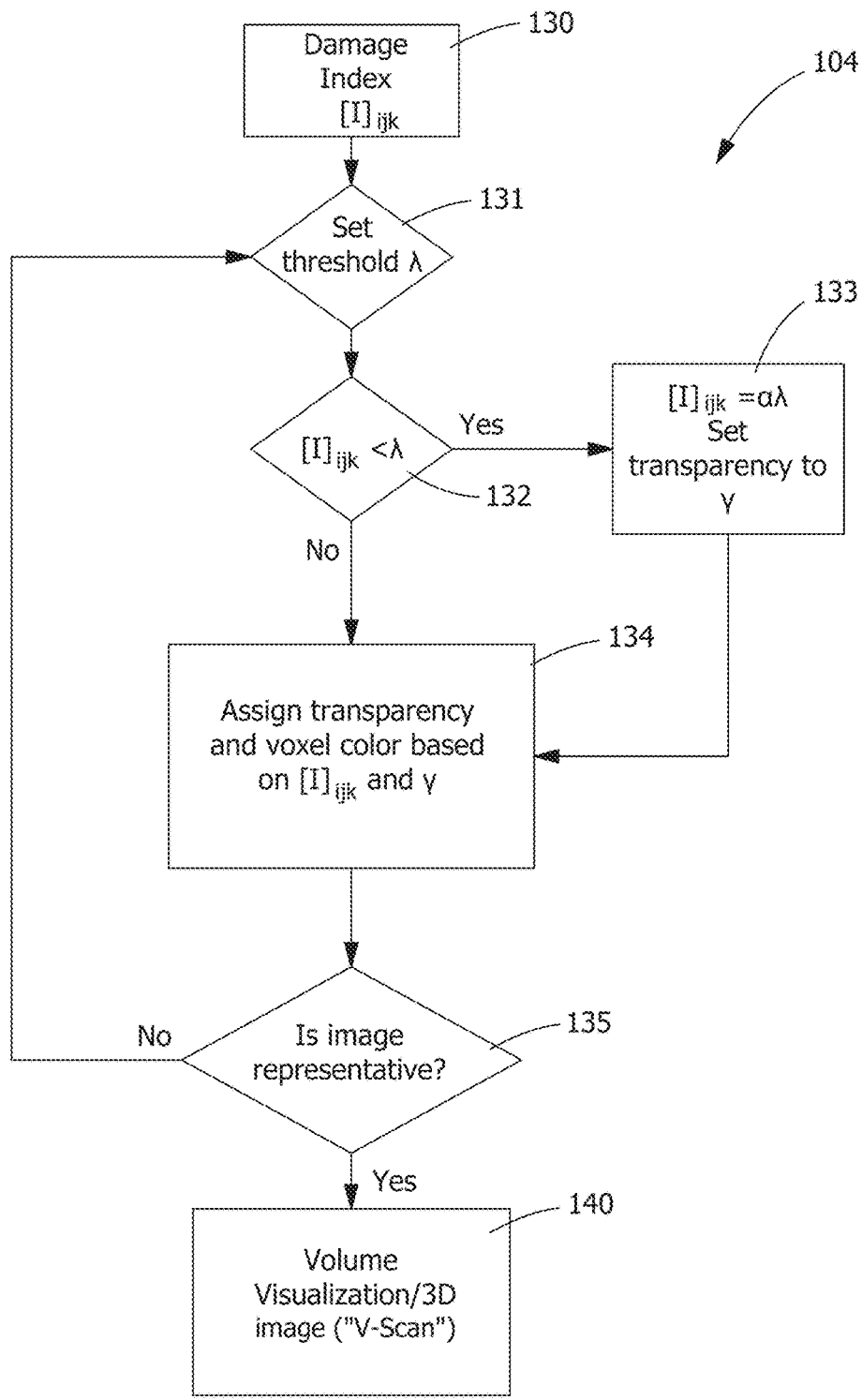
FIG. 6 is a flowchart of the volume visualization of the method of FIG. 3.
Figure 19:
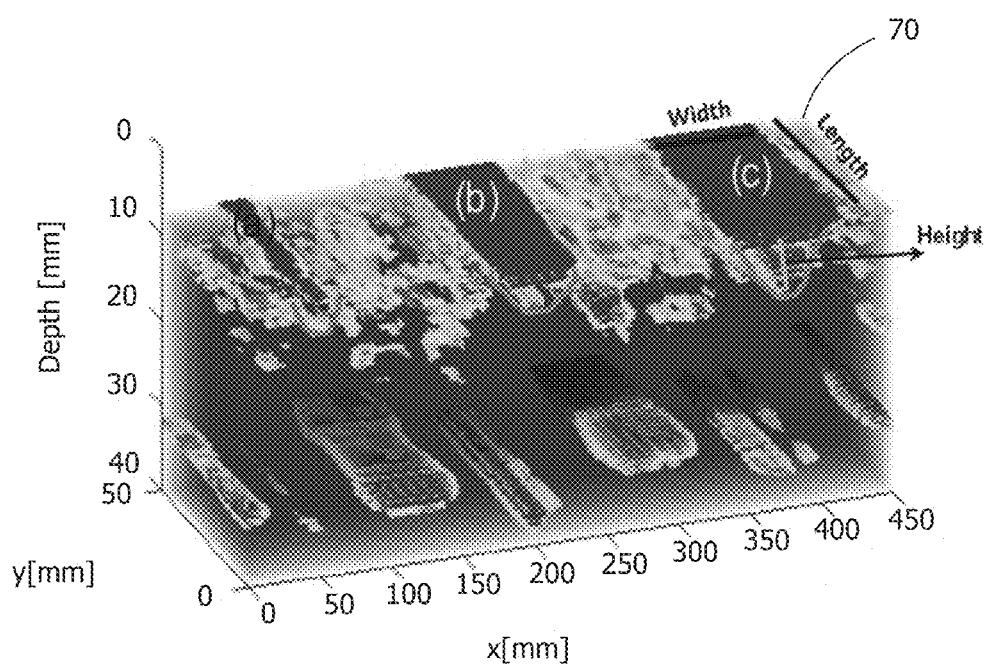
FIG. 19 is a V-scan image of the test panel with waviness of FIG. 2 from methods of the present disclosure.
Figure 21:
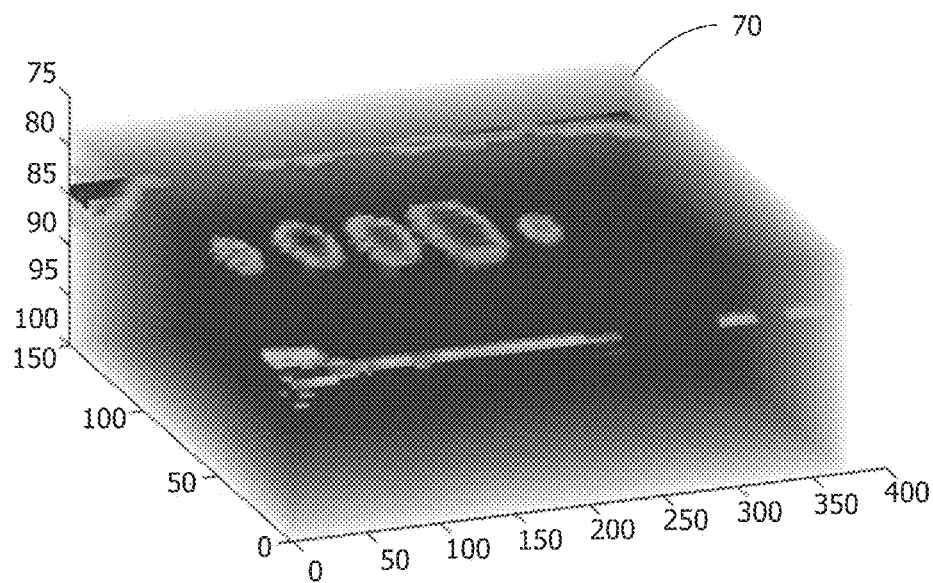
FIG. 21 is a V-scan image of the test panel with debonding of FIG. 18 from methods of the present disclosure.

Referring to FIG. 6, volume visualization (step 104) is based on the damage index values 130 assigned to the various voxels during feature extraction (step 103). In the V-scans shown in FIG. 19 and FIG. 21, the damage index values 130 range from 0 to 1 and correspond to colors ranging from blue to red. This color map may, of course, change based upon the operator's preferences. For volume visualization, a threshold damage index value is selected 131, and each voxel having a value exceeding the threshold value is assigned a color based on its damage index value. Each damage index value is compared to the threshold value 132. If the damage index value is less than the threshold value, the voxel is considered not part of a feature, but rather than being colorless and transparent, the voxel is assigned a color based on its location 133 in order to give a three-dimensional perception to the V-scan image. If the damage index value is not less than the threshold value, the voxel is assigned a color based on the damage index value of the voxel 134. The areas in various levels of blue in FIG. 19 and FIG. 21 represent voxels outside the feature areas. The resultant V-scan image is then evaluated 135. If the resultant V-scan image 70 is not representative, the volume visualization process may be repeated by selecting a different threshold value by trial and error until a representative image is produced. If the resultant V-scan image 70 is representative, the generation of a V-scan image 140 is considered to be complete.

Figure 7:
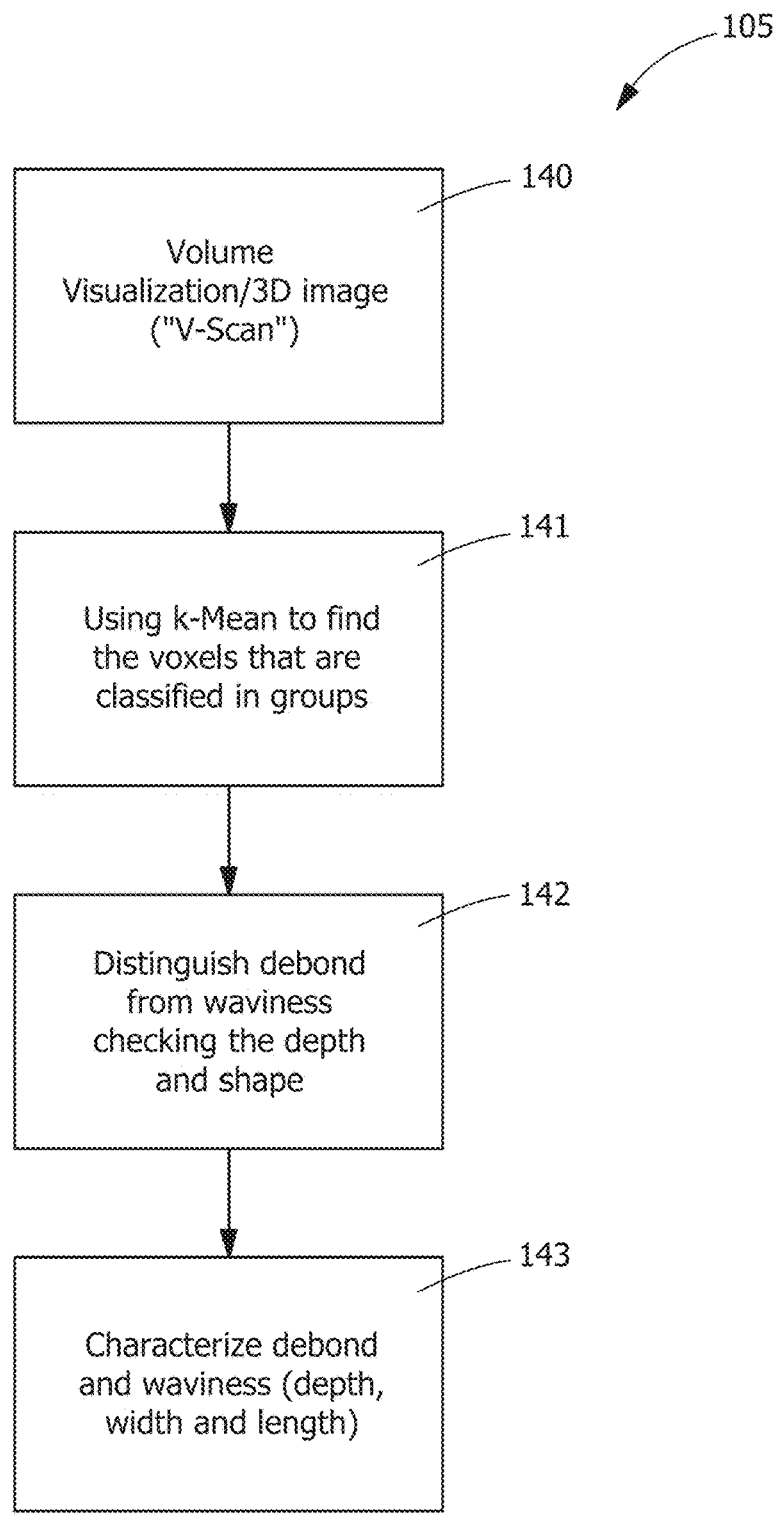
FIG. 7 is a flowchart of the clustering/recognition and characterization of the method of FIG. 3.

Referring to FIG. 7, after generation of a V-scan image 140 from the volume visualization, a clustering method classifies voxels in groups based on their color values (step 141). In some embodiments, the clustering method is k-mean clustering. The depth and the shape of the groups are then used to identify and distinguish debonding features from waviness features (step 142). In some embodiments, a height of the feature is used to distinguish a debonding feature from a waviness feature, with waviness features having a height greater than a predetermined value and debonding features having a height less than the predetermined value. The debonding features and waviness features are preferably characterized (step 143) such as, for example, by one or more dimensions, including, but not limited to, their depth, width, length, or combinations thereof. As waviness and debonding of a composite layered structure may significantly reduce its strength, detection and characterization of these features (step 105) is an important first step in determining the expected strength of the composite layered structure.

Figure 8:
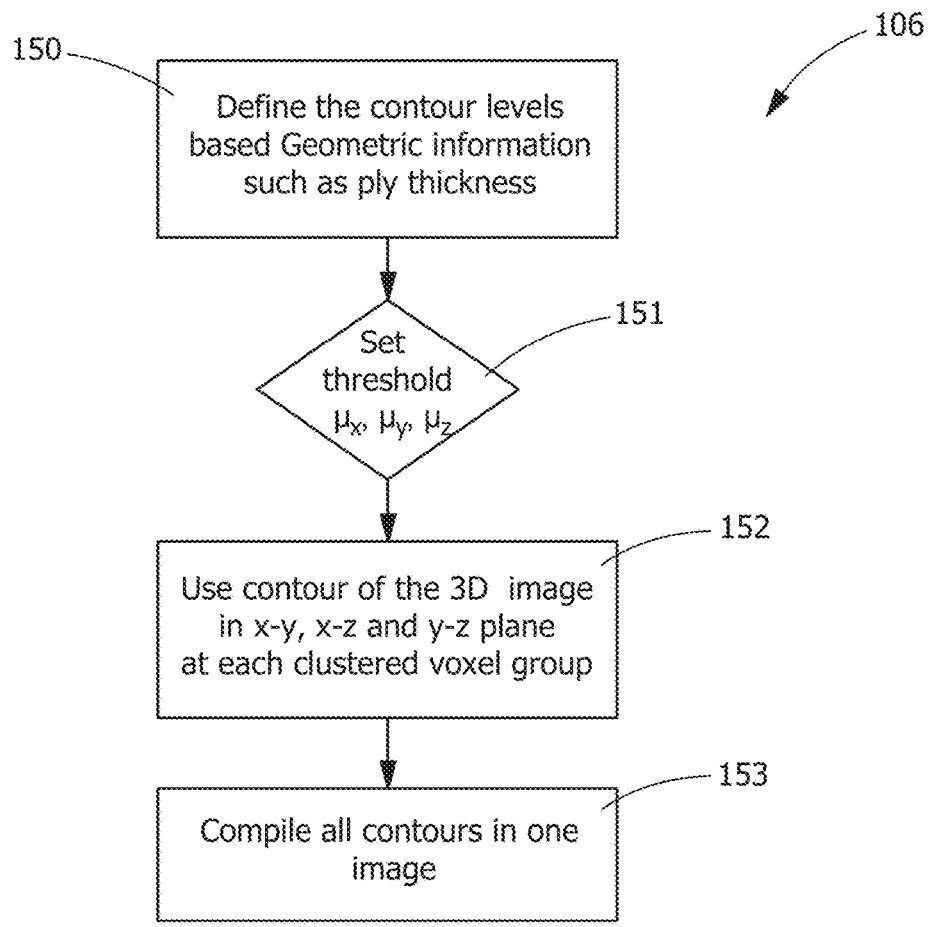
FIG. 8 is a flowchart of the data compression of the method of FIG. 3.
Figure 20:
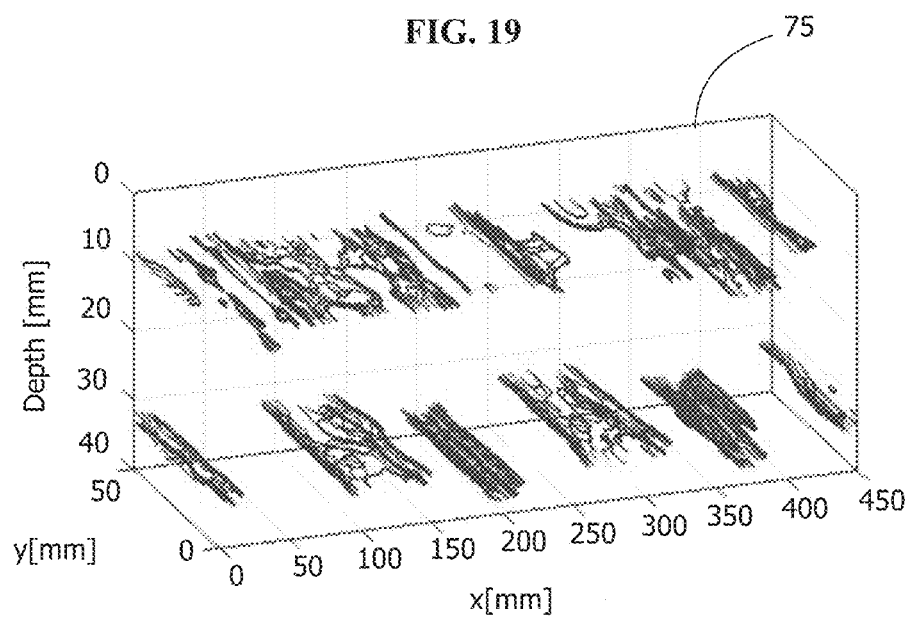
FIG. 20 is a 3-D contour extraction of the V-scan image data of FIG. 19 from methods of the present disclosure.
Figure 22:
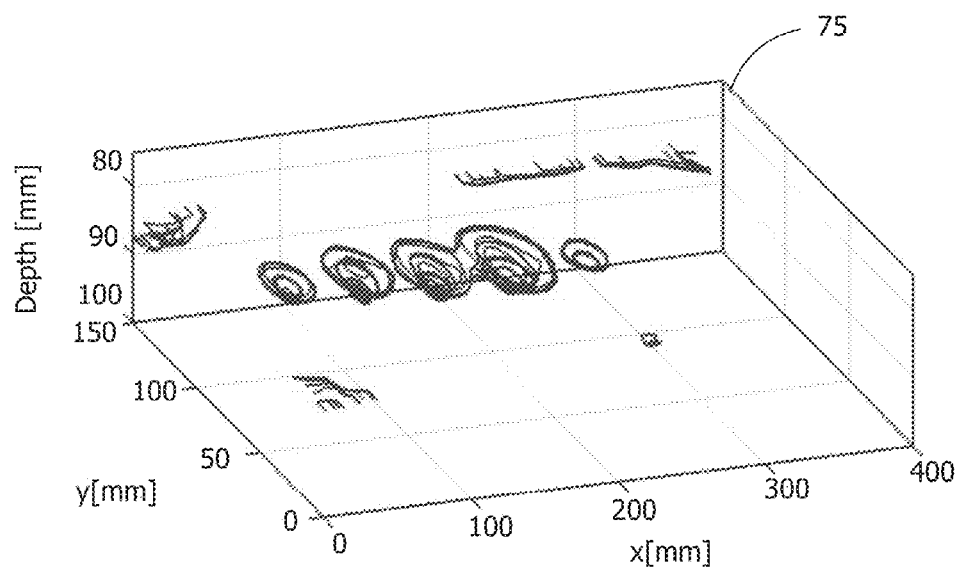
FIG. 22 is a 3-D contour extraction of the V-scan image data of FIG. 21 from methods of the present disclosure.

Referring to FIG. 8, data compression (step 106) may be used to reduce the data size for alternative visualization, for long-term data storage, or for further data analysis, such as by finite element method software. The data compression preferably includes defining contour levels (step 150) based on geometric information, such as layer thickness, setting a threshold value for the contour lines (step 151), defining the contour of the 3-D image (V-scan) in x-y, x-z, and y-z planes at each clustered voxel group (step 152), and compiling all contours into a single image (step 153). All scaling by color is preferably removed by the data compression 106. FIG. 20 and FIG. 22 show border tracing images based on contours from data compression.

The data from conventional ultrasound test (UT) imaging, e.g. B-scan and C-scan, was investigated for the detection and characterization of out-of-plane waviness and 3-D volume visualization in order to enhance the detection and characterization of this type of out-of-plane waviness by ultrasound. The 3-D UT volume images described herein may be created from UT C-scan waveforms extracted from commercially-available UT scanners.

In some embodiments, the component 16 with the visually-inaccessible structure 18 to be detected is a wind turbine blade. In some embodiments, the visually-inaccessible structure 18 is a spar cap. The wind turbine blade may include multiple layers between the spar cap and the outer surface of the blade. In some embodiments, the wind turbine blade includes an outer finishing layer, a priming layer under the finishing layer, a shell under the priming layer, a spar under the shell, the spar cap under the spar, and a shear web under the spar cap. The finishing may be polyurethane paint. The priming may be a UV gelcoat layer. The shell may be a pre-preg material. The spar may be a glass fiber or carbon fiber material. The shear web may be a pre-preg material.

In other embodiments, the component 16 is an aircraft composite component of the aircraft frame. Aircraft composite components may include, but are not limited to, composite laminates, carbon fiber sandwiches, and fiberglass. In other embodiments, the component 16 is a helicopter composite component, which may include, but is not limited to, helicopter blades including continuous glass fiber reinforced epoxy matrix composites. In other embodiments, the component 16 includes a pressure vessel including a fiber composite. In other embodiments, the component includes a boat hull.

Examples

Figure 9:
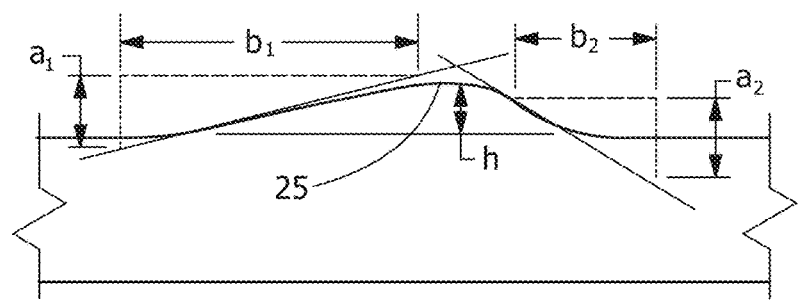
FIG. 9 is a schematic side cross-sectional view of a waviness feature showing aspect ratio parameters.

In order to evaluate and validate the UT detectability and the ability to characterize out-of-plane waviness, three mock-up panels with internal waviness of various aspect ratios (ARs) were used. Referring to FIG. 9, the AR is defined as the minimum of the AR values ($AR_1$ and $AR_2$) of the two sides of the wave 25. The AR values of the two sides of the wave 25 are defined as twice the inverse of the slope of the wave 25, or $AR_1=2b_1/a_1$ and $AR_2=2b_2/a_2$, as indicated in FIG. 9. The slopes (a/b) of the wave are preferably measured at half the height of the wave on each side of the wave.

All three mock-up panels were constructed to evaluate the UT capability to detect and characterize waviness in carbon composite spar caps. The wave panels were fabricated using the nominal maximum spar cap thickness for 48.7-meter blades of approximately 33 mm. Each panel included 55 plies of 0.6-mm thick carbon layers. In order to represent typical waves, two different types of waviness were fabricated. Waviness in Panel 1 and Panel 2 was constructed from resin; waviness in Panel 3 was fabricated using a layered laminate to achieve the intended ARs. The height of the waves was held constant at 3 mm in order to keep the panel size manageable for the larger AR waves. Three separate ARs, (a) AR=5, (b) AR=15, and (c) AR=25, were built. The range of ARs allowed the inspection results to be correlated with the actual wave height. The characteristics of the Panels 1-3 are listed in the Table 1.

TABLE 1

Geometry of Waviness Test Panels

| Panel Number | Waviness | Aspect Ratio | Starting Ply | Process |
|---|---|---|---|---|
| 1 | a | 5 | 45 (27 mm) | Resin wave |
|  | b | 15 | 45 (27 mm) | Resin wave |
|  | c | 25 | 45 (27 mm) | Resin wave |
| 2 | a | 5 | 10 (6 mm) | Resin wave |
|  | b | 15 | 10 (6 mm) | Resin wave |
|  | c | 25 | 10 (6 mm) | Resin wave |
| 3 | a | 5 | 28 (17 mm) | Pre-preg wave |
|  | b | 15 | 28 (17 mm) | Pre-preg wave |
|  | c | 25 | 28 (17 mm) | Pre-preg wave |

The material properties and ultrasonic characteristics of the resin and cured fiber composites in the z-direction are listed in Table 2.

TABLE 2

Material Properties of Waviness Test Panels

| Material | Bulk wave velocity [m/s] | Density [kg/m$^3$] | Module elasticity in z-direction [MPa] | Ultrasonic impedance [kg/(s × m$^2$)] × 10$^6$ |
|---|---|---|---|---|
| Resin | 1682.4 | 1180 | 3340 | 1.98 |
| Cured carbon fiber composites | 2307.5 | 1540 | 8200 | 3.55 |

X-Ray Computed Tomography (CT) Results

CT scans were conducted on the wave mock-up panels using a GE Optima CT660 (GE Healthcare). The three panels were stacked on top of each other to reduce the scanning time. Furthermore, a wood panel was placed on top of the three specimens to improve the quality of CT images. The axial scanning resolution was set to be 2 mm and the current intensity was selected based on trial and error to achieve the maximum resolution. The CT inspection protocol included a voltage of 140 kV at a current of 350 mA.

Figure 10:
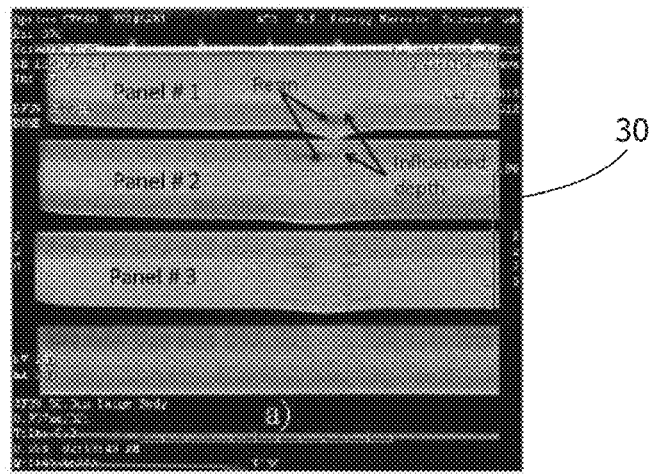
FIG. 10 is a radial cross-sectional side view CT scan image of waviness type a) of the three panels of Table 1.
Figure 11:
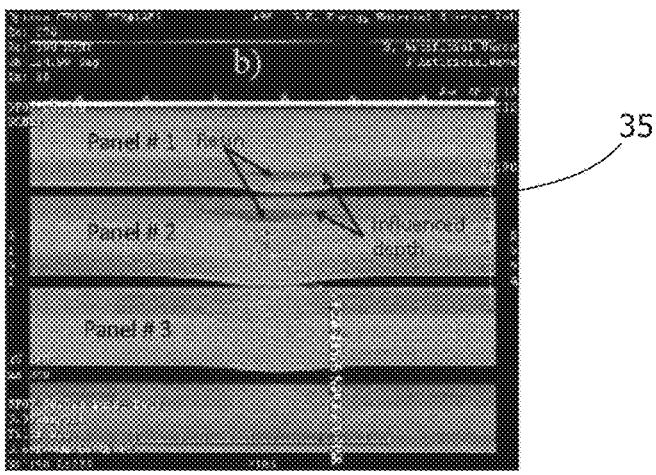
FIG. 11 is a radial cross-sectional side view CT scan image of waviness type b) of the three panels of Table 1.
Figure 12:
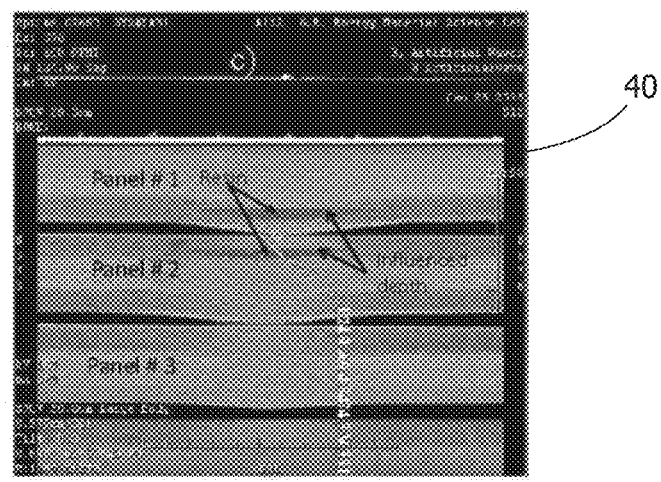
FIG. 12 is a radial cross-sectional side view CT scan image of waviness type c) of the three panels of Table 1.
Figure 13:
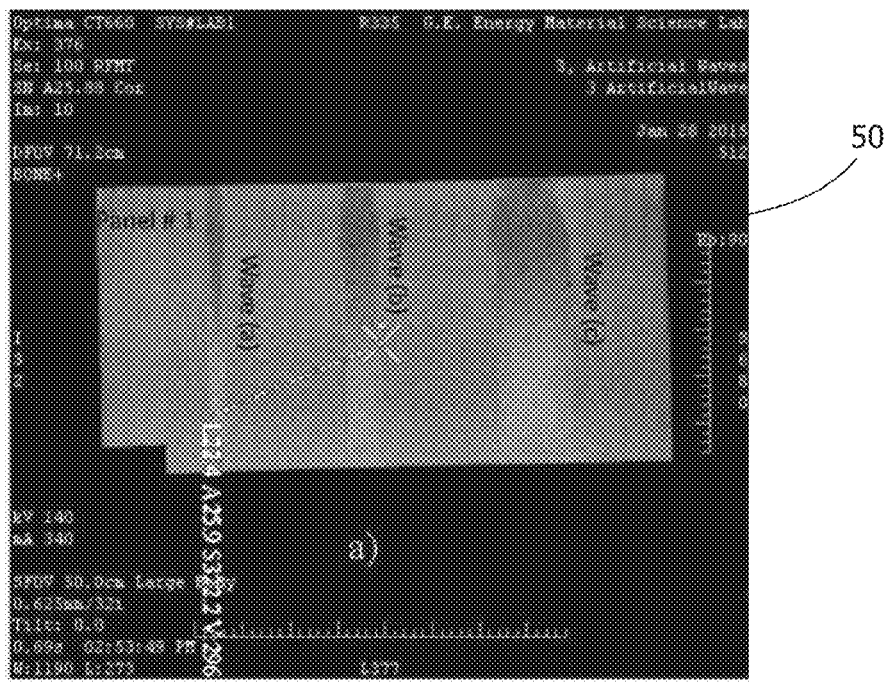
FIG. 13 is a top view CT scan image of Panel 1 at the wave starting depth.
Figure 14:
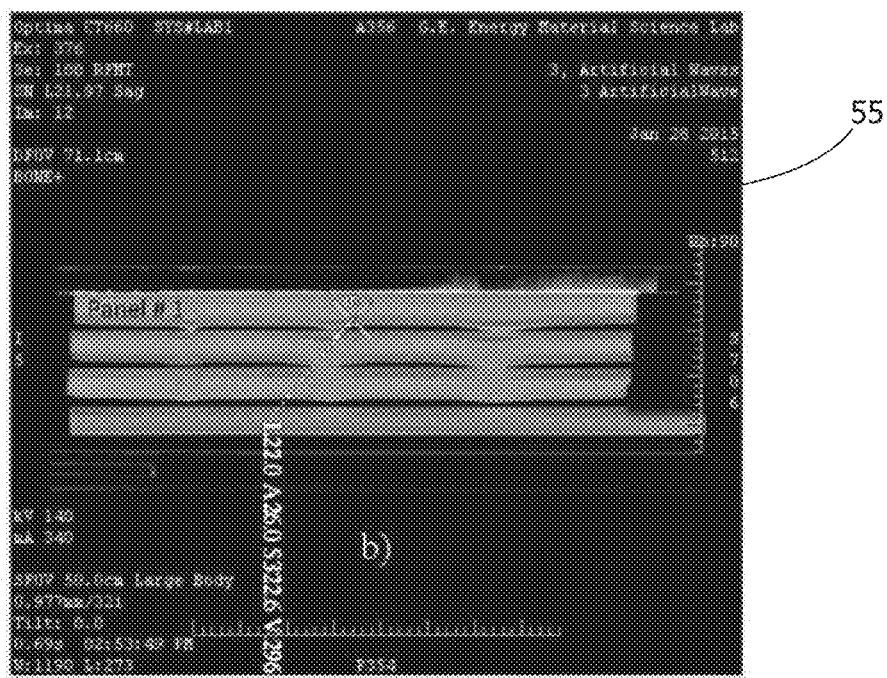
FIG. 14 is a radial cross-sectional side view of the three panels of Table 1 at the slice position indicated in FIG. 13.
Figure 15:
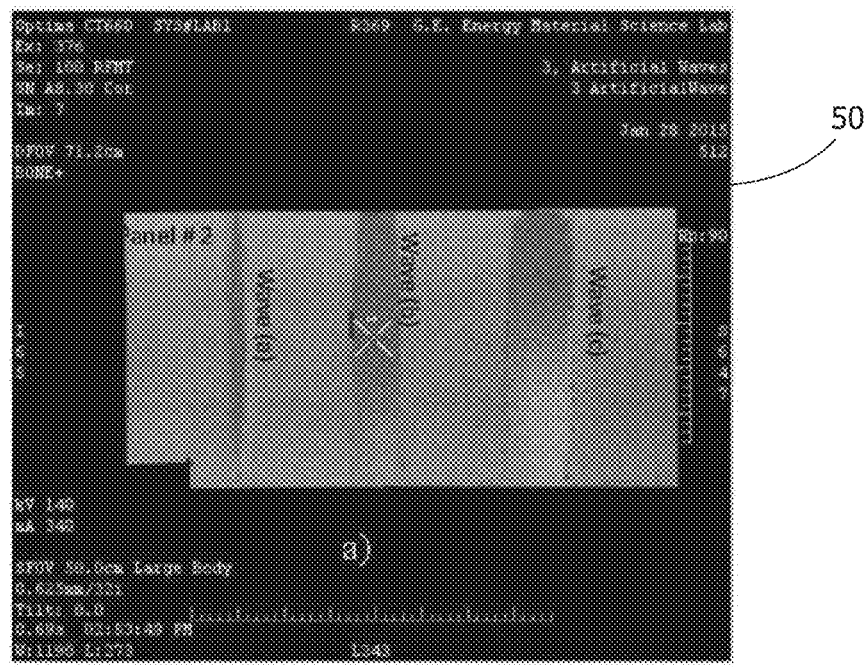
FIG. 15 is a top view CT scan image of Panel 2 at the wave starting depth.
Figure 16:
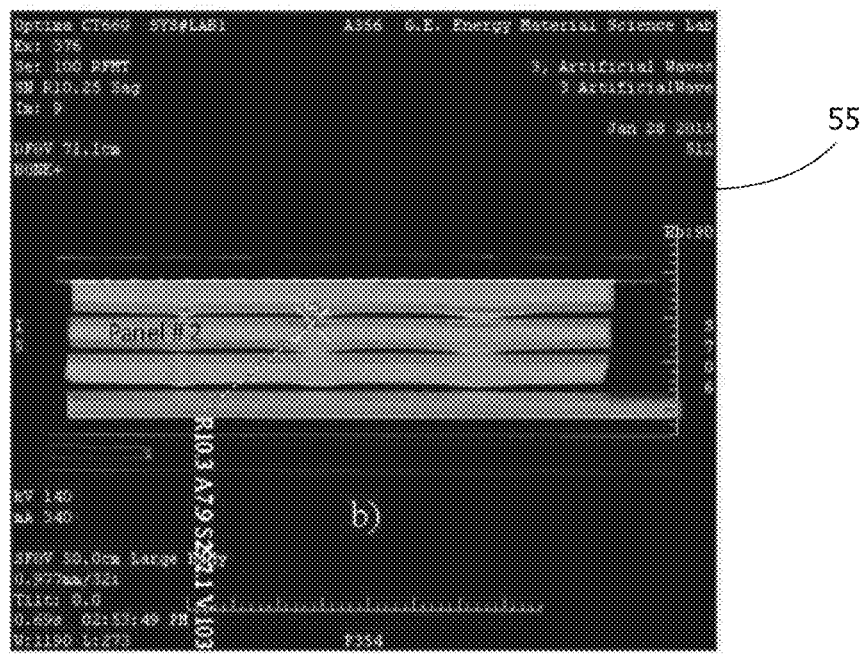
FIG. 16 is a radial cross-sectional side view of the three panels of Table 1 at the slice position indicated in FIG. 15.

Referring to FIG. 10, FIG. 11, and FIG. 12, the CT images 30, 35, and 40, respectively, show the three types of waviness of Table 1, namely waviness (a), waviness (b), and waviness (c), respectively. The resin wave samples (Panel 1 and Panel 2) were clearly distinguished, since the density of the resin is much less than the surrounding cured carbon fiber material. In contrast, the second type of waviness that was created using a pre-impregnated composite fiber (pre-preg) material (Panel 3) was not detected in the CT image 35 unless it appeared on the panel surface.

The number of impacted layers and the aspect ratio of the waviness was measured in the case of resin waves. Referring to FIG. 13, FIG. 14, FIG. 15, and FIG. 16, the width and height of all three waves (a), (b), and (c) were measured in the CT images 50 and 55, respectively, for the first two panels, even if they did not appear on the surface of the panel. This, however, was not the case for the third panel, since the first affected layer was not detected from the CT image cross section.

UT Experimental Set-Up

Figure 2:
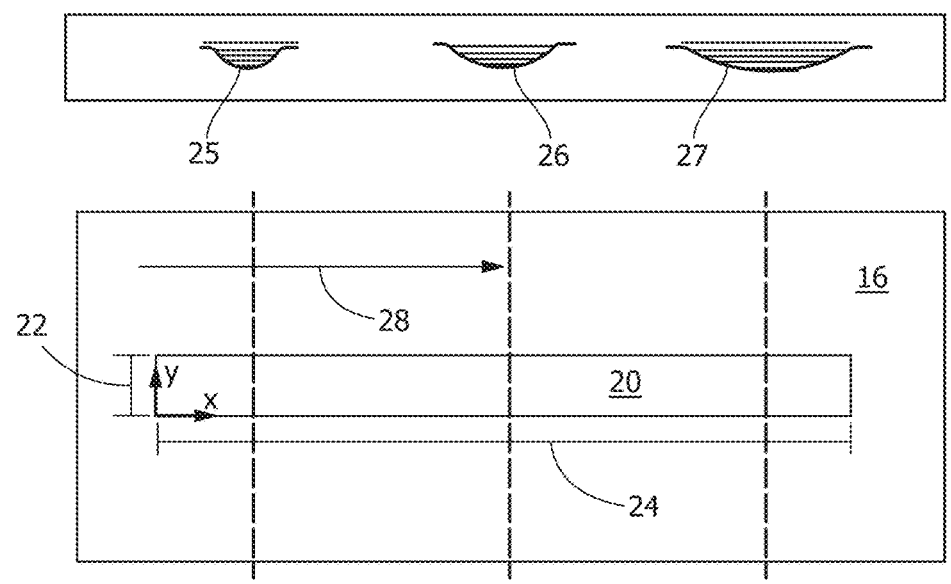
FIG. 2 is a schematic side view and a schematic top view of a test panel with waviness for detection by methods of the present disclosure.

Experiments were conducted to evaluate the ability of conventional UT B-scans and C-scans with a volume visualization to characterize the implanted waviness. The middle section of each component 16 was scanned to decrease test time, as shown schematically in FIG. 2. The scan area 20 for the C-scans covered a width 22 of about 50 mm and a length 24 of about 450 mm. The scan area 20 crossed all three waves, wave (a) 25, wave (b) 26, and wave (c) 27, of the component 16, with the visually-inaccessible feature of the component 16 having a fiber direction 28 as indicated by the arrow in FIG. 2.

The scan resolution was set at 1 mm in the x-direction and 2 mm in the y-direction. Two different 1-inch diameter transducers with 500-kHz and 1-MHz resonance frequencies were used in order to evaluate the signal-to-noise ratio, resolution, and sensitivity of the different frequencies. A square wave pulse enhanced the signal-to-noise ratio. The sampling frequency was set at 10 MHz to reduce the data file size. Water was used as a couplant. A little soap was added to the couplant to break the water tension and reduce the friction in order to have a uniform distribution of couplant on the specimen's surface and ease the scanning process. A two-channel UT tablet and a manual x-y scanner (Mistras Group, Inc., Princeton Junction, N.J.) were used for data acquisition. Following each scan, the data was saved and exported to comma-separated values (CSV) file format for post-processing proposes. A MATLAB program was developed to analyze and generate the volume visualization of extracted UT data. Near field effects at both 500 kHz and 1 MHz were discounted, because this simplified the test procedure and avoided multiple wedge reflections, and the detection and characterization of waves was intended to be based only on B-scan and C-scan image information.

Panel 1 UT Results

In some embodiments, waviness is characterized by estimating one or more of three values: a waviness AR, the depth or number of affected plies, and the chordwise extent. B-scans on Panel 1 produced 2-D images for both the 500 kHz and the 1 MHz transducers. The waviness of all three waves (a), (b), and (c) was detected if the wave appeared on the surface of the spar cap. The out of plane waviness (resin waves) was detected not only from its indication on the back wall, which is a result of waviness on the surface, but also from internal reflection and scattering of the ultrasound at the start of the wave due to a mismatch of ultrasonic impedance of the resin wave and its surroundings. A comparison of 500 kHz and 1 MHz B-scans showed that a 1 MHz transducer provides better resolution and detection capability than a 500 kHz transducer. For Panel 1, the overall B-scan results of the 1-MHz transducer provided valuable information on the AR and the depth of influenced laminates.

C-scan images of the two slices at start of the waviness and at the back wall were examined. It was clear that the C-scan at the start of the waviness that was detected in the B-scan may be used to measure the chordwise extent of the waviness if, and only if, the waviness is completely horizontal.

The presence of a shadow in the back-wall C-scan in the waviness locations was an indication of waviness detection.

The width of the shadow increased as the AR increased. It should be noted, however, that the use of back wall shadowing as an indication for waviness detection may be significantly compromised if the wave does not appear on the back wall surface. Furthermore, the effect of a convex or concave shape of the waviness on the reflection and scattering of sound may negatively or positively affect the presence of a shadow on the back-wall C-scan.

Multiple C-scans were piled at different depths to generate a 3-D view. Although this 3-D view of the scans gave a better understanding of the waviness characteristics, it was not able to show the chordwise extension of the waviness in the case of partial waves. Furthermore, if the geometry of the waviness is complex, such as for an inclined internal wave, then the B-scans and C-scans cannot be easily used for waviness characterization.

Volume visualization, as used herein, is a sophisticated imaging tool that significantly enhances the detection and characterization of features with complex geometry, such as waviness. As used herein, the volume visualization of UT data is referred to as a V-scan. Wave detection and characterization were significantly enhanced using volume visualization of the Panel 1 UT data.

In order to extract quantitative information regarding the waviness and also reduce the size of the image, a contour-extraction program of border tracing was developed and applied to the V-scan image. In border tracing, a threshold is set to determine the 2-D border of the wavy feature. Applying the same program for different C-scans and compiling the borders in 3-D view provided the quantitative and transferable results of a V-scan with reasonable data size.

Panel 2 UT Results

The main difference between Panel 2 and Panel 1 was the starting depth of the waviness. In Panel 2, the first influenced laminate was much closer to the surface. UT scans were performed on Panel 2 similar to Panel 1. The out of plane resin waves (a), (b), and (c) were detected in a B-scan not only from their indication on the back wall, which resulted from the appearance of the waviness on the surface, but also from internal reflection and scattering of the ultrasound at the start of the wave due to a mismatch of the ultrasonic impedance of the resin wave and its surroundings. The detection in this case was much better than for Panel 1, since the wave was closer to the surface, resulting in higher reflection amplitude. A comparison of the 500 kHz B-scan with the 1 MHz B-scan led to the conclusion that the 1-MHz transducer provides better resolution and detection capability. The overall B-scan results of both the 500-kHz and the 1-MHz transducer provided the valuable information of the AR and the depth of influenced laminates.

Figure 17:
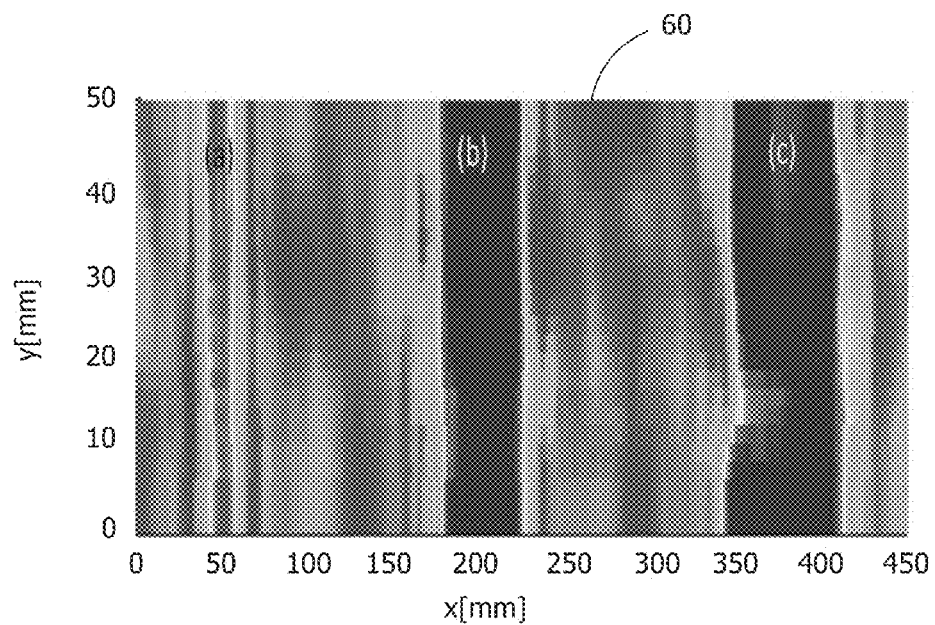
FIG. 17 is a UT C-scan image of the test panel of FIG. 2.

The C-scan image 60 of the slice at the start of the waviness is shown in FIG. 17 for the 500-kHz transducer. The C-scan at the start of the waviness that was detected in the B-scan was used to measure the chordwise extent of the waviness, but this is accurate if, and only if, the waviness is completely horizontal.

Similarly to the scans for Panel 1, the presence of shadowing in the back-wall C-scan in the waviness locations for Panel 2 was used as an indication for waviness detection. The width of the shadow increased as the AR increased. The use of the back wall shadow, however, as an indication for waviness detection is significantly compromised if the wave does not appear on the back wall surface. Furthermore, the effect of a convex or concave shape of the waviness on the reflection and scattering of sound may negatively or positively affect the presence of shadowing in the back-wall C-scan.

The V-scan images 70, as shown in FIG. 19 and FIG. 21 for the 1-MHz transducer, were much more informative than conventional B-scans and C-scans. As the depth of the waviness features is determined from the V-scan 70, it is easy to distinguish the features as waviness features, as the depth of the features is too large for them to be debonding features. A clear image of the back wall and the wave shapes is very helpful in waviness detection and characterization. Even features with complex geometries are detected and characterized more reliably than with conventional UT imaging in the form of B-scans and C-scans.

The border tracing 75 from the contour extraction for the 1-MHz data is shown in FIG. 20. In some embodiments, the border tracing 75 compresses the data size by more than an order of magnitude as compared to the V-scan 70 data. In one embodiment, the V-scan data 70 was about 12 MB in size and the related border tracing 75 data was only about 0.8 MB in size. This method results in a better structural evaluation where precise geometric information is needed by design engineering for modeling the feature.

Panel 3 UT Results

The waviness in the Panel 3 is a pre-preg wave and the starting affected laminate is in the middle of the panel. The waviness is detected from the back wall indications, since the wave appears on the surface of the back wall. However if the pre-preg wave were internal and did not appear on the back wall, it would be detected. The main reason for this limitation is that the sound impedance of the wave is almost the same as the surroundings, making the reflection coefficient very small.

There is no indication of waviness from the C-scan at the start of the waviness. The shadow indicating the presence of the waviness, however, is visible in the back wall scan. The back-wall reflection is very weak due to the scattering of the sound close to the surface. There are two separate regions in the B-scan for Panel 3. It seems that the panel has two separate regions with different material qualities. This separation was observed in the CT image as a shaded area on top of Panel 3. This situation might be much worse in the field and may result in a missed detection of waviness, even if it appears on the back wall surface.

In general, a carbon composite material is inhomogeneous and the quality of material may vary drastically. The sound reflection characteristics may change when moving the transducer from one location to another, which affects the B-scan and C-scan images. For example, the B-scan of Panel 3 at y=17 mm was found to be different than the B-scan at y=1 mm. Waviness detection in carbon composite spar caps is highly dependent on the quality of material, as the material properties significantly affect the ultrasound propagation characteristics. Another observation based on the B-scan of Panel 3 at y=17 mm is that although the linear UT scanning (B-scan) may increase the test speed, it is more prone to a misdetection of partial waves than a full x-y UT scan, because a partial wave does not extend all over the chord.

From the V-scan image of Panel 3, the two regions were clearly distinguishable. Furthermore, contrary to the B-scan, the waviness misdetection problem is less likely if the UT V-scan image is used.

Debonding Detection of a Model Spar Cap with Debonding

Similar UT scans and data processing were performed for a model spar cap with debonding. The model spar cap included five areas of debonding of different degrees spaced about 50 mm (about 2 in.) apart in a row along a top plane of the model spar cap. The model spar cap was covered by a model wind turbine blade shell and the model spar cap was detected by ultrasound through the model wind turbine blade shell.

Figure 18:
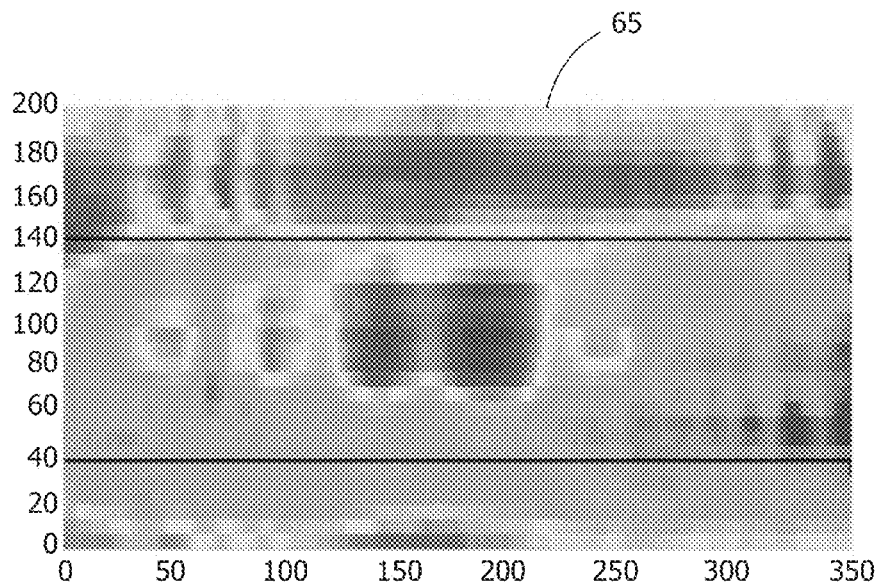
FIG. 18 is a UT C-scan image of a test panel with debonding.

FIG. 18 shows a C-scan image 65 of the debonding in the model spar cap. FIG. 21 shows a V-scan image 70 of the model spar cap with debonding. As the depth of the debonding features is determined from the V-scan image 70, it is easy to distinguish the features as debonding features rather than waviness features. FIG. 22 shows the border tracing 75 from the contour extraction of the model spar cap with debonding.

In summary, B-scan and C-scan data from conventional UT imaging was processed for detection and characterization of out-of-plane waviness. Furthermore, a 3-D volume visualization, termed a V-scan herein, enabled the detection and characterization of out-of-plane waviness.

A wide range of waviness with different ARs may be detected if the wave appears on the surface of a spar cap. Although waviness appearing on the surface of the spar cap may easily be detected using visual inspection, in some cases visual inspection may be compromised, and the visual inspection is very difficult to perform after manufacturing.

The out-of-plane waviness, such as resin waves, may be detected not only from an indication on the back wall resulting from waviness on the surface, but also from internal reflection and scattering of the ultrasound at the start of the wave due to a mismatch of ultrasonic impedance of the resin wave and its surroundings.

Overall, in case of a resin wave, the B-scan results may provide valuable information on the AR and the depth of influenced laminates.

In general, a 1-MHz transducer was found to provide better resolution and detection capability than a 500-kHz transducer. Although higher frequency transducers enhance the image resolution, they are more sensitive to voids and porosity. As a result, it is recommended that the frequency be selected based on the composite material quality in the field to achieve maximum signal-to-noise ratio.

Although a B-scan may increase the test speed, it is more prone to a misdetection of partial waviness (where the partial wave does not extend all over the chord) than a C-scan.

A C-scan image may give information about the width and chordwise extent of a resin wave. The presence of shadowing in the back-wall C-scan in the waviness locations may be used as an indication for waviness detection.

In general, waviness with a larger AR was found to be easier to detect than waviness with a smaller AR.

The results of volume visualization (V-scan) are more informative than conventional B-scans and C-scans. Features with complex geometries are detected and characterized more reliably with a V-scan than with the conventional UT imaging, such as B-scans and C-scans.

Border tracing 75 provides quantitative and transferable results of V-scan with a reasonable reduced data size relative to the V-scan data size. Border tracing 75 results in a better structural evaluation where precise geometric information is needed by design engineering for modeling a feature.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A method of non-destructive testing, the method comprising:
   locating an ultrasonic transducer with respect to a component having a visually-inaccessible structure to collect B-scan data from at least one B-scan of the component and to collect C-scan data from at least one C-scan of the component;
   filtering the B-scan data and the C-scan data to remove random noise and coherent noise based on predetermined geometric information about the visually-inaccessible structure to obtain filtered data; and
   performing linear signal processing and nonlinear signal processing to determine a damage index for a plurality of voxels representing the visually-inaccessible structure from the filtered B-scan data and the filtered C-scan data.

2. The method of claim 1 wherein the predetermined geometric information comprises a layer thickness of the visually-inaccessible structure.

3. The method of claim 1 further comprising generating ea volume visualization as a V-scan image of V-scan data from the damage index.

4. The method of claim 3 wherein generating the volume visualization comprises assigning each voxel falling below a threshold damage value a color value based on a location of the voxel to provide a three-dimensional effect to the V-scan image.

5. The method of claim 3 further comprising extracting a three-dimensional contour from the V-scan data and calculating a strength of the component based on the volume visualization or the three-dimensional contour.

6. The method of claim 1 wherein the visually-inaccessible structure comprises a fiber composite.

7. The method of claim 1 wherein the visually-inaccessible structure comprises a composite laminate.

8. The method of claim 1 wherein the component comprises a wind turbine blade and the visually-inaccessible structure comprises a spar cap.

9. The method of claim 1 further comprising quantifying at least one characteristic of at least one feature of the visually-inaccessible structure selected from the group consisting of a location of waviness, a depth of waviness, a length of waviness, and an aspect ratio of waviness of the feature.

10. An ultrasound system comprising:
    at least one ultrasonic transducer; and
    a computer operatively connected to the ultrasonic transducer, wherein the computer is configured to:
        direct the ultrasonic transducer to conduct at least one B-scan and collect B-scan data from the at least one B-scan and to conduct at least one C-scan and collect C-scan data from the at least one C-scan of a component comprising a visually-inaccessible structure;
        filter the B-scan data and the C-scan data to remove random noise and coherent noise based on predetermined geometric information about the visually-inaccessible structure to obtain filtered data; and
        perform linear signal processing and nonlinear signal processing to determine a damage index for a plurality of voxels representing the visually-inaccessible structure from the filtered B-scan data and the filtered C-scan data.

11. The ultrasound system of claim 10 wherein the computer is further configured to quantify at least one characteristic of the visually-inaccessible structure selected from the group consisting of a location of out-of-plane waviness, a depth of out-of-plane waviness, a length of out-of-plane waviness, and an aspect ratio of waviness.

12. A method of non-destructive testing, the method comprising:
locating an ultrasonic transducer with respect to a component having a visually-inaccessible structure to collect B-scan data from at least one B-scan of the component and to collect C-scan data from at least one C-scan of the component;
filtering the B-scan data and the C-scan data to remove random noise and coherent noise based on predetermined geometric information about the visually-inaccessible structure to obtain filtered data;
performing linear signal processing and nonlinear signal processing to determine a damage index for a plurality of voxels representing the visually-inaccessible structure from the filtered B-scan data and the filtered C-scan data;
generating a volume visualization as a V-scan image of V-scan data from the damage index; and
clustering the plurality of voxels based on damage index values and characterizing at least one feature in the visually-inaccessible structure as a debonded feature or a waviness feature by distinguishing a debonded state and a waviness state of the visually-inaccessible structure.

13. The method of claim 12 wherein the predetermined geometric information comprises a layer thickness of the visually-inaccessible structure.

14. The method of claim 12 wherein generating the volume visualization comprises assigning each voxel falling below a threshold damage value a color value based on a location of the voxel to provide a three-dimensional effect to the V-scan image.

15. The method of claim 12 wherein the waviness feature comprises an out-of-plane waviness.

16. The method of claim 12 further comprising performing a data compression comprising defining contour levels of clustered voxels, setting a contour threshold value for contour lines, defining a contour of a 3-D image in x-y, x-z, and y-z planes at each clustered voxel group, and compiling the contours into a single contour image comprising the contours.

17. The method of claim 12 further comprising quantifying at least one characteristic of at least one feature of the visually-inaccessible structure selected from the group consisting of a location of waviness, a depth of waviness, a length of waviness, and an aspect ratio of waviness of the feature.

18. The method of claim 12 further comprising extracting a three-dimensional contour from the V-scan data.

19. The method of claim 18 further comprising calculating a strength of the component based on the volume visualization or the three-dimensional contour.

20. An ultrasound system comprising:
at least one ultrasonic transducer; and
a computer operatively connected to the ultrasonic transducer, wherein the computer is configured to:
direct the ultrasonic transducer to conduct at least one B-scan and collect B-scan data from the at least one B-scan and to conduct at least one C-scan and collect C-scan data from the at least one C-scan of a component comprising a visually-inaccessible structure;
filter the B-scan data and the C-scan data to remove random noise and coherent noise based on predetermined geometric information about the visually-inaccessible structure to obtain filtered data;
perform linear signal processing and nonlinear signal processing to determine a damage index for a plurality of voxels representing the visually-inaccessible structure from the filtered B-scan data and the filtered C-scan data;
generate a volume visualization as a V-scan image of V-scan data from the damage index;
extract a three-dimensional contour from the V-scan data; and
determine a presence of debonding or waviness of the visually-inaccessible structure from the volume visualization or the three-dimensional contour.

21. The ultrasound system of claim 20 wherein the computer is further configured to quantify at least one characteristic of the visually-inaccessible structure selected from the group consisting of a location of out-of-plane waviness, a depth of out-of-plane waviness, a length of out-of-plane waviness, and an aspect ratio of waviness.

* * * * *